United States Patent [19]

Noce et al.

[11] Patent Number: 4,960,127
[45] Date of Patent: Oct. 2, 1990

[54] DISPOSABLE TRANSDUCER MANIFOLD

[75] Inventors: Louis O. Noce; Michael Basta, both of Longwood, Fla.

[73] Assignee: L.O.N. Research, Inc., Sanford, Fla.

[21] Appl. No.: 299,500

[22] Filed: Jan. 23, 1989

[51] Int. Cl.$^5$ .............................................. A61B 5/02
[52] U.S. Cl. .................................... 128/675; 128/748
[58] Field of Search .............................. 128/672–675, 128/748; 73/706, 708, 715, 756

[56] References Cited

U.S. PATENT DOCUMENTS

| | | | |
|---|---|---|---|
| 4,198,989 | 4/1980 | Hawke et al. | 128/675 |
| 4,505,157 | 3/1985 | Hong Le | 128/675 X |
| 4,539,998 | 9/1985 | McCord et al. | 128/675 |
| 4,610,256 | 9/1986 | Wallace | 128/675 |
| 4,679,567 | 7/1987 | Hanlon et al. | 128/675 |
| 4,776,343 | 10/1988 | Hubbard et al. | 128/675 |
| 4,819,653 | 4/1989 | Marks | 128/673 |
| 4,825,876 | 5/1989 | Beard | 128/675 |

OTHER PUBLICATIONS

"Motorola Semiconductor Technical Data", MPX2040D, MPX2050, MPX2051, Motorola Inc., 1988.
"Healthcare Industry . . . Manufacturers", Sensors, Feb. 1985.
"For Hemodynamic . . . Disposable VTM Manifolds", Namic.
"Medex Low Profile Domes", Medex Inc.
"Novotrans–The Perfect Transducer", Novatrans, Feb. 1984.
"Components", Medi-Trace Pressure Monitoring Systems.
"Disposable Pressure Transducer System", Medi-Trace.
"DTX Disposable Transducer Systems", Gould.

Primary Examiner—Max Hindenburg
Assistant Examiner—J. P. Lacyk
Attorney, Agent, or Firm—Nixon & Vanderhye

[57] ABSTRACT

A disposable transducer manifold assembly is provided which includes a tubular manifold formed within a frame and having an inlet and provided with at least one sensing port. The sensing port is enclosed by a chamber defined by a housing integrally formed within said frame. A pressure sensing transducer in the form of a microchip sensor is located within said housing such that a sensing surface is adapted for direct exposure to fluid in said tubular manifold through said sensing port. Electrical cable connection means are provided which extend outwardly from the housing for electrically connecting the pressure sensing transducer to a monitor.

25 Claims, 1 Drawing Sheet

DISPOSABLE TRANSDUCER MANIFOLD

FIELD OF THE INVENTION

This invention relates generally to pressure sensing in medical applications and, more specifically, to an improved method and apparatus for hemodynamic pressure sensing and monitoring.

BACKGROUND AND SUMMARY OF THE INVENTION

In conventional hemodynamic pressure sensing and monitoring systems, a catheter from the heart or other location is connected to a tubular manifold and frame assembly which is provided with one or more valved ports. Flexible plastic tubing extends from the manifold ports of the assembly (which is typically attached to the patient's arm, chest, etc.) to one or more pressure sensor and monitoring devices. Each pressure sensor includes a transducer dome and transducer, typically mounted on a vertical post located about six feet away from the patient. In this arrangement, blood passing into and/or through the manifold may be periodically diverted via conventional petcock type valves through a pressure monitoring tube connected between one of the manifold ports and the post-mounted pressure sensor.

However, this arrangement is not completely satisfactory for a number of reasons. Most significantly, the frequency response or resolution of the pressure readings are affected by the length and durometer of the pressure monitoring tubing, the composition of the tubing and so on. In other words, any distortion or change in flexibility of the tubing (which is normally constructed of a flexible plastic material) as a result of temperature changes, for example, will impact on the accuracy of the pressure readings. As a result, the apparatus must be re-calibrated often to compensate for such changes.

A further requirement to obtain accurate readings is that the transducer must be mounted at substantially the same height as the patient to avoid the effects of gravity. This requirement necessitates additional equipment which permits the pressure transducer to be vertically adjusted on the pole or stand.

The above-described conventional systems require periodic manipulation of the manifold petcocks when readings are desired. This, of course, presents a danger of leakage and resulting contamination of persons and/or things in the immediate area.

The present invention provides a method and apparatus which eliminates the aforementioned problems associated with conventional hemodynamic pressure monitoring systems.

In an exemplary embodiment of the present invention, a pressure sensing transducer is mounted directly within the manifold assembly. The transducer includes a microchip enclosed within a gel, effectively directly exposed to blood flowing into the manifold. This construction has many advantages, one of which is the ability to continuously sense and monitor pressure. The chip itself is preferably permanently joined and sealed to the manifold, and connection means are provided so that an electrical cable, connected to a monitor, can be easily connected or disconnected from the manifold assembly. In this regard, an O-ring seal is preferably employed between the transducer chip and the manifold to prevent the escape of fluid from around the sensor.

The transducer per se is not part of this invention and, in a preferred embodiment, is a microchip sensor commercially available pressure sensor manufactured by Motorola, the details of which are specified herein. This invention relates to the arrangement of the sensor within a manifold assembly, such that pressure may be continuously sensed and monitored without danger of leakage.

As noted above, the present invention has numerous advantages over prior art pressure sensing systems. For example, the present invention provides a simple, easy to use, highly accurate and significantly less costly pressure monitor which eliminates the conventional transducer dome and pressure monitoring tubing.

In addition, since the manifold including the sensor may be attached directly to the patient, the concern for the effects of gravity, is substantially eliminated.

Another advantage lies in the fact that the time consuming recalibration efforts caused by changes in the plastic monitoring tubing, primarily as a result of temperature changes, are also eliminated. In this regard, the preferred microchip sensor includes an automatic temperature compensation and recalibration circuit so that, to the extent periodic calibration is required, it is done automatically.

The present invention also confines the blood within the manifold, thereby reducing the risk of contamination present in prior art systems where the blood must flow through the lengthy monitoring tube to reach the post-mounted sensor.

Another advantage of the present invention is that the entire assembly, including the transducer, is easily disposed of after each use.

It will be appreciated that the sensor/manifold arrangement of this invention may be incorporated into a single port manifold, or in a multi-port manifold where one or more of the remaining ports may contain conventional valving arrangements. Of course, one or more of the additional ports may also incorporate the sensor in accordance with this invention.

Thus, the present invention in accordance with one embodiment comprises a disposable transducer manifold assembly for hemodynamic pressure monitoring comprising:
  a manifold frame;
  a hollow, tubular manifold formed within said frame and having an inlet at one end for receiving fluid;
  at least one sensing port provided in the tubular manifold;
  a pressure sensing transducer mounted adjacent the port, a sensing surface of the transducer adapted for direct exposure to fluid in the tubular manifold; and
  connector means extending from the pressure sensing transducer.

In a related aspect, the present invention provides a method for continuously monitoring blood pressure comprising the steps of:
  providing a tubular manifold having an inlet at one end and at least one sensing port;
  permanently securing a pressure sensing transducer directly to the manifold such that a pressure sensing surface of the transducer is exposed directly to blood in the manifold through the sensing port;
  sealing the pressure sensing surface relative to the manifold; and providing electrical cable means for connection between the manifold and a monitor device.

Additional objects and advantages of the present invention will become apparent from the detailed description which follows.

DETAILED DESCRIPTION OF THE DRAWINGS

Figure 1:
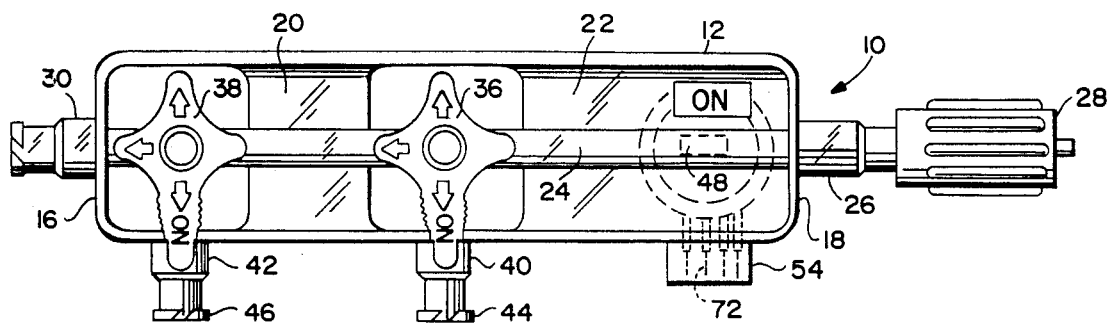
FIG. 1 is a plan view of the disposable transducer manifold assembly in accordance with one exemplary embodiment of the invention.
Figure 2:
FIG. 2 is a partial side view of the assembly of FIG. 1, partially sectioned to illustrate the interior of the manifold assembly.
Figure 3:
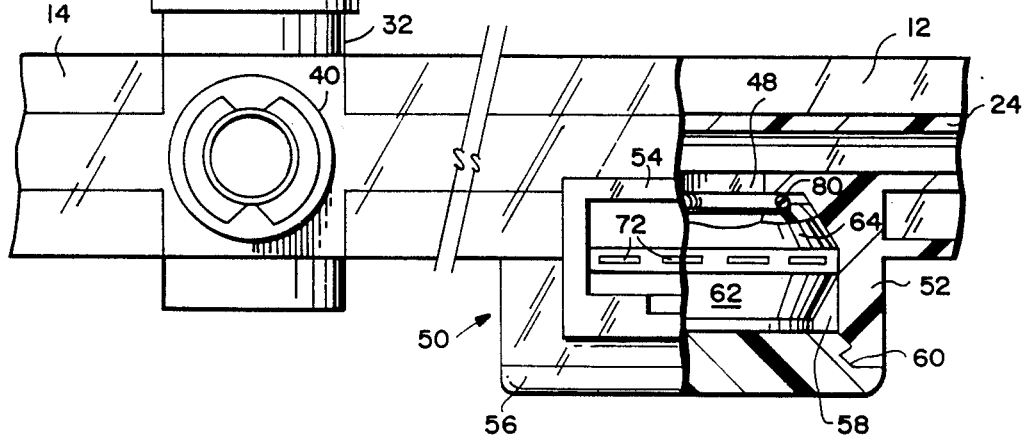
FIG. 3 is an end view of the assembly illustrated in FIG. 1, also partially sectioned to illustrate the interior of the manifold assembly.

With reference particularly to FIGS. 1 through 3, the disposable transducer manifold assembly of this invention includes, in one exemplary embodiment, a manifold frame 10 comprised of a rectangular unit which includes side walls 12, 14 and end walls 16, 18 and substantially flat reinforcing webs 20, 22 extending between the frame walls at a location substantially midway of the height thereof.

A hollow tubular manifold 24 extends from end wall 16 to end wall 18, the longitudinal axis thereof extending substantially coplanar with the reinforcing webs 20, 22. At an inlet end of the manifold assembly, an inlet extension 26 is provided which slidably receives a conventional coupling member 28 for attachment to a catheter or the like, supplying blood from the patient to the manifold. An outlet end of the manifold assembly includes an outlet extension 30 which may be connected to a return tube or capped, depending on the particular application of the device.

Extending from upper and lower surfaces of the tubular manifold 24 are a pair of valve ports, one of which is shown at 32. These ports telescopically receive conventional petcocks 36, 38 which contain rotatable valves as are well understood in the art. Outlet ports 40, 42 are integrally joined to the valve ports, such that each petcock 36, 38 can direct blood from the tubular manifold through a respective outlet 40 or 42, or when rotated, direct fluid through both the outlets 40, 42 and the manifold outlet 30, or through the tubular manifold outlet 30, bypassing the respective outlet ports 40, 42 in a manner well understood by those skilled in the art.

Each outlet port 40, 42 is formed with an enlarged coupling portion 44, 46, respectively, adapted to receive flexible plastic tubes which carry blood from the manifold to a sensing/monitoring or other treatment station.

In this exemplary embodiment, all elements described hereinabove with the exception of the slidable coupling 28 and petcocks 36, 38 are formed as an integral molded unit, preferably constructed of a transparent polycarbonate plastic material.

In further accord with this exemplary embodiment, a third outlet or sensing port 48 is provided in the form of a rectangular aperture in a lower surface of the tubular manifold 24. This port is surrounded by a first housing portion 50, which is also integrally molded to the frame. Specifically, the first housing portion 50 includes a substantially annular wall 52 which joins the frame at the undersurface of the reinforcing web 22. A substantially rectangular shroud portion 54 extends outwardly from the annular wall 54 in a direction substantially parallel to the outflow direction of ports 40, 42. A lower cap portion 56 may be snapped or otherwise fastened to the annular wall 52 so that a substantially hollow chamber 58 is formed, open at the rectangular shroud portion 54. Suitable friction type fastening surfaces, shown at 60, may be employed to hold the cap 56 to the housing portion 52, preferably with the aid of a suitable adhesive.

Enclosed within the chamber 58 is a pressure sensing transducer 62. In this exemplary embodiment, the transducer 62 is preferably a Motorola MPX 2040D (Case 344-03) microchip pressure sensor which has an on-chip automatic temperature compensation and calibration circuit. The sensor includes a thermoplastic case 64, a metal back plate 66, a microchip 68, and wires 70 extending from the microchip to a corresponding number of the leads or prongs 72 which extend away from the case 64. The microchip 68 is itself enclosed within a gel 74 formed with a concave sensing surface 76. The thermoplastic case 64 is further provided with a counterbore which forms a flat surface 78 on which rests an O-ring 80, for a purpose described hereinbelow.

The microchip 68 is supported on a board (not shown) which, in turn, is supported on the metal plate 66 permanently secured within the case 64. An aperture 82 is formed within the plate 66 and an aligned aperture 84 is formed in the case 64 to vent the interior of the transducer 62 to atmosphere.

It will be understood that other suitable pressure sensing transducers may be utilized in conjunction with the invention. For example, in a similar transducer to that described herein, it is possible to employ a diaphragm in place of the gel 74 to act as the pressure sensing surface.

It will be appreciated that prior to the attachment of cap 56 to the first housing portion 52, the transducer 62 is located within the housing so that leads or prongs 72 (of which there are four) extend outwardly within the shroud portion 54 which encloses and protects the leads. Upon application of the cap 56, the pressure sensor 62 is pressed into engagement with the under surface of the web 22 in surrounding relationship to the aperture 48 formed in the tubular manifold 24 as best seen in FIG. 3. It will thus be appreciated that the concave pressure sensing surface 76 is exposed directly to blood in the tubular manifold 24 via the aperture 48. At the same time, the O-ring 80 prevents the escape of fluid past the pressure sensor and out of the manifold assembly.

Figure 4:
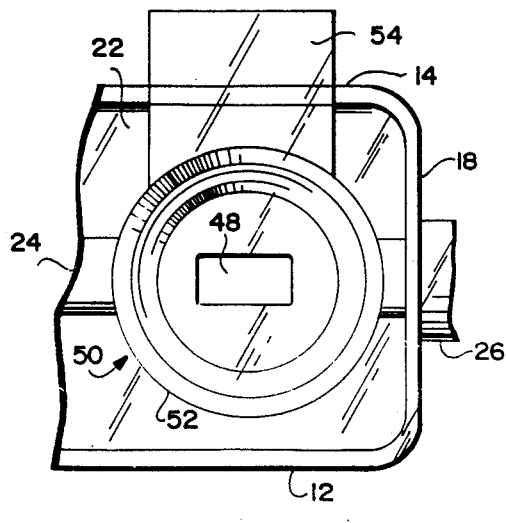
FIG. 4 is a partial bottom view of the assembly shown in FIG. 1, but with a cap and transducer removed.

With reference to FIG. 4, it will be appreciated that leads or prongs 74 are easily connectable to a plug and associated cable (not shown) which electrically connect the manifold/sensor assembly to a monitor (not shown).

In use, the above-described disposable transducer manifold assembly may be utilized in a continuous blood pressure sensing and monitoring process. In accordance with this invention, the process comprises the steps of (a) providing a tubular manifold 24 having an inlet at one end and at least one sensing port 48;

(b) permanently securing a pressure sensing transducer 62 directly to the manifold such that a pressure sensing surface 76 of the transducer 62 is exposed directly to blood in the manifold through the sensing port 48;

(c) sealing the pressure sensing surface 76 relative to the sensing port 48; and (d) providing electrical cable means for connection between the manifold and a monitor device. It will be understood, of course, that other manifold configurations are within the scope of this invention. For example, any combination of conventional ports, and ports according to this invention may be provided within the manifold frame. Single port manifolds, i.e., frames with a single port 48 and associated sensor 62, are also contemplated by the invention.

It will be further understood that while the present invention has been described in the context of hemodynamic pressure sensing/monitoring, the invention has ready application in other comparable fluid pressure sensing arrangements, e.g., in neurological, urological and respiratory monitoring systems which include measurements of intracranial pressures, gastroenterological measurements, uterine pressure, bladder pressure, hemodialysis, intraocular pressure, and so on.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A disposable transducer manifold assembly for fluid pressure monitoring comprising:
    an elongated manifold frame;
    a hollow, elongated tubular manifold formed within and at least coextensive with said frame and having an inlet end for receiving fluid directly from a patient, an outlet end for returning said fluid to the patient and a substantially axial passageway extending between said inlet and outlet ends;
    at least one valve port and at least one sensing port provided in the tubular manifold intermediate said inlet and outlet ends, and opening into said passageway;
    a pressure sensing transducer mounted within a housing at least partially molded into said manifold frame adjacent said sensing port, a sensing surface of said transducer adapted for direct exposure to fluid flowing through said passageway across said sensing port; and
    electrical connector means extending from said pressure sensing transducer to a monitor.

2. A disposable transducer manifold assembly according to claim 1 wherein said pressure sensing transducer comprises a microchip surrounded by a gel exposed directly to said fluid.

3. A disposable transducer manifold assembly according to claim 1 wherein said pressure sensing transducer comprises a microchip exposed indirectly to said fluid via a diaphragm.

4. A disposable transducer manifold assembly according to claim 2 wherein said gel is formed with a concave sensing surface.

5. A disposable transducer manifold assembly according to claim 1 wherein said pressure sensing transducer comprises a microchip surrounded by a gel composition, said gel composition providing a sensing surface, and wherein sealing means are provided which surround said sensing surface and said sensing port, to prevent leakage of fluid from said assembly through said sensing port.

6. A disposable transducer manifold assembly according to claim 1 wherein said manifold frame is provided with a plurality of sensing ports.

7. A disposable transducer manifold assembly according to claim 1 wherein said tubular manifold is closable at an end opposite said one end.

8. A disposable transducer manifold assembly according to claim 1 wherein said sensing port comprises an aperture in said tubular manifold and wherein said transducer lies adjacent said aperture and is surrounded by sealing means which prevents leakage of fluid from said sensing port.

9. A disposable transducer manifold assembly according to claim 1 wherein said housing includes an integrally molded shroud portion formed in said manifold frame, and wherein said electrical connector means extend from said transducer and are partially enclosed by said shroud portion.

10. A disposable transducer manifold assembly comprising:
    an elongated frame;
    an elongated tubular manifold formed within said frame and having an inlet end and an outlet end, said tubular manifold defining an axial fluid passageway between said inlet and outlet ends, said tubular manifold provided with and at least one sensing port and at least one valve port in communication with said passageway;
    a pressure sensing transducer located directly over said at least one sensing port, said sensing transducer enclosed within an integral housing portion of said frame, said pressure sensing transducer comprising
    a microchip sensor encased within a gel composition which provides a sensing surface, said sensing surface adapted for direct contact with fluid flowing over said sensing port in said axial fluid passageway of said tubular manifold.

11. Hemodynamic pressure sensing apparatus comprising:
    a hollow, elongated tubular manifold integrally molded within a frame and defining an axial fluid passageway, said tubular manifold having an inlet at one end thereof; at least one sensing port and at least one valve port open to said fluid passageway formed within said tubular manifold; a housing portion integrally formed with said tubular manifold and surrounding said sensing port; a cap portion fixed to said housing portion to form a chamber; a pressure sensing transducer mounted within said chamber such that a pressure sensing surface lies adjacent and in communication with, said sensing port; resilient sealing means interposed between said housing portion and said pressure sensing transducer and surrounding said sensing port to prevent leakage of fluid from said tubular manifold; and electrical leads extending from said sensing transducer, through said housing portion.

12. Hemodynamic pressure sensing apparatus according to claim 11 wherein said sealing means comprises an O-ring.

13. Hemodynamic pressure sensing apparatus according to claim 12 wherein said housing portion is formed with an outwardly extending shroud for partially enclosing said electrical leads.

14. Hemodynamic pressure sensing apparatus according to claim 11 wherein said pressure sensing transducer comprises a microchip which includes a temperature compensation and recalibration circuit.

15. Hemodynamic pressure sensing apparatus according to claim 11 wherein said tubular manifold, said frame, said housing portion and said cap portion are comprises of plastic.

16. A process for continuous monitoring of blood pressure in a patient comprising the steps of:
(a) providing a frame having a tubular manifold integrally formed therein and extending axially between opposite ends of said frame, said tubular manifold having an inlet end, an outlet end, at least one sensing aperture and at least one valve port located intermediate said inlet and outlet ends;
(b) permanently securing a pressure sensing transducer within a housing portion of said manifold frame such that a pressure sensing surface of said transducer is aligned with said sensing port and thus exposed directly to blood flowing through said manifold by means of said at least one sensing aperture;
(c) sealing said pressure sensing surface relative to said tubular manifold about said aperture; and
(d) providing electrical cable means for connection between said manifold and a monitor device.

17. A process according to claim 16 wherein the tubular manifold is mountable directly on the patient and the inlet is connected to a catheter supplying blood from said patient to the manifold.

18. A process according to claim 16 wherein said pressure sensing transducer comprises a microchip sensor.

19. A process according to claim 18 wherein said pressure sensing transducer includes a gel composition encasing said microchip, said gel forming said sensing surface.

20. A process according to claim 16 wherein said sealing step includes providing an O-ring between said pressure sensing surface and said manifold in surrounding relationship to said at least one sensing aperture.

21. A disposable transducer manifold assembly comprising: an elongated rectangular frame having a pair of side walls, a pair of end walls;
a tubular manifold integrally formed with said frame and extending between said end walls, said tubular manifold having an inlet and an outlet at each of said end walls, respectively;
a plurality of laterally spaced reinforcing webs extending between said side walls and said tubular manifold;
a housing portion integrally formed in said frame within at least one of said reinforcing webs, said housing portion including an interior chamber;
at least one sensing port provided in said tubular manifold opening into said interior chamber of said housing portion;
a transducer mounted within said interior chamber with a sensing surface located adjacent said sensing port; and
at least one valve port formed in said tubular manifold and including a valve located within said valve port and operable to control flow of liquid through said tubular manifold 22. A disposable transducer manifold assembly according to claim 21 wherein said valve comprises a three-way petcock.

23. A disposable transducer manifold assembly according to claim 21 wherein three sensing ports are provided in said tubular manifold, each of said ports having a three-way valve associated therewith.

24. A disposable transducer manifold assembly according to claim 21 and including an electrical connector and associated cable extending from said transducer.

25. A disposable transducer manifold assembly according to claim 21 wherein said frame, said tubular manifold, said reinforcing webs and said housing portion are constructed of transparent plastic material.

* * * * *